United States Patent [19]

Crugnola et al.

[11] 4,404,327

[45] Sep. 13, 1983

[54] ORTHOPAEDIC CEMENT FROM ACRYLATE POLYMERS

[76] Inventors: Aldo M. Crugnola, 51 Frederick St., Unit 85, Dracut, Mass. 01826; Edward J. Ellis, 109 Jackman St., Georgetown, Mass. 01969

[21] Appl. No.: 353,597

[22] Filed: Mar. 1, 1982

Related U.S. Application Data

[63] Continuation of Ser. No. 89,933, Oct. 31, 1979, abandoned.

[51] Int. Cl.$^3$ .................... C08L 33/12; C08L 33/08
[52] U.S. Cl. ............................... 525/228; 525/309; 525/304; 525/288; 525/209; 523/115; 523/116
[58] Field of Search ............... 523/116, 115; 433/228; 525/309, 228

[56] References Cited

U.S. PATENT DOCUMENTS

| | | | |
|---|---|---|---|
| 2,947,716 | 8/1960 | Cornell et al. | 525/228 |
| 3,649,608 | 3/1972 | Logemann et al. | 525/228 |
| 3,681,475 | 8/1972 | Spilner | 525/81 |
| 3,758,642 | 9/1973 | Logemann et al. | 525/228 |
| 4,159,288 | 6/1979 | Carson et al. | 525/228 |
| 4,182,035 | 1/1980 | Yamauchi et al. | 523/116 |
| 4,220,582 | 9/1980 | Orlowski et al. | 523/116 |
| 4,341,691 | 7/1982 | Anuta | 523/116 |

*Primary Examiner*—Carman J. Seccuro
*Attorney, Agent, or Firm*—Pearson & Pearson

[57] ABSTRACT

An improved orthopaedic cement of the type used to, e.g. position and hold prosthetic devices in place within bone cavities after surgical repair of the bone system. The cement is characterized by markedly increased toughness and resistance to fracture due to the rubbery, or elastomeric, nature of the included polyacrylate resin phase.

10 Claims, No Drawings

ORTHOPAEDIC CEMENT FROM ACRYLATE POLYMERS

This is a continuation of our application Ser. No. 089,933, filed Oct. 31, 1979, now abandoned.

BACKGROUND OF THE INVENTION

This invention relates to the field of prosthetic orthopaedic devices and assemblies and, in particular, to a novel orthopaedic cement.

All joints in the human body are subject to destruction by disease and trauma. The goal of skeletal prostheses is permanent, functional replacement of bone and joints which have failed. Polymeric materials have shown great promise as orthopaedic implants. In fact, one of the more successful orthopaedic implants is the total hip system where the acetabular component is ultra High molecular weight polyethylene (UHMWPE) and the femoral component is a metallic alloy. Acrylic cement is generally utilized in the fixation of the prosthesis components.

Acrylic cements were first developed for dental uses about 30 years ago and were subsequently modified for orthopaedic use. These cements are not adhesive. They function by mechanical interlocking with surrounding porous bone structure.

Composition of Acrylic Bone Cement: The composition of a typical acrylic cement would be:

| Liquid Component | % by Volume | Powder Component | % by Weight |
|---|---|---|---|
| methyl methacrylate | 97.5 | polymethyl methacrylate* | 88 |
| N,N—dimethyl toluidine | 2.5 | benzoyl peroxide | 2 |
| Hydroquinone | 75 ppm | barium sulfate | 10 |

*or mixture of polymethyl methacrylate (PMMA) with copolymers of methyl methacrylate (MMA) and minor amounts of styrene of other methacrylate monomer.

The cement is supplied to the surgeon in kit form which typically contains a 20 ml ampule of sterile monomer liquid and a 40 gm pouch of sterile polymer powder. It should be noted that for proper handling characteristics the polymer powder is generally composed of spherical particles or mixtures of spherical particles with irregularly shaped particles. The particle size is usually less than 200 mesh with diameters typically in the 10 to 30 micron range.

During surgery the cement is prepared by mixing the liquid and powder components. Within a few minutes (4–5) the cement becomes dough-like and is ready, at this point, to be worked into the bone cavity. The prosthesis is then inserted and aligned. The cement hardens in about 10 to 15 minutes to fix the device in place. The time intervals between the various stages of cement consistency depend on the particular product and ambient conditions at the surgical site.

After polymerization, or "hardening", the cement contains approximately 2 to 5% residual monomer and has considerable entrapped air. The powder particles are retained so that the polymerized cement is actually a composite material wherein PMMA particles are dispersed in a newly polymerized PMMA matrix. The physical properties of existing prosthetic acrylic cements are lower than those of conventional PMMA polymer.

|  | Acrylic Cement | Commercial PMMA |
|---|---|---|
| compressive str, psi | 9,000–14,000 | 11,000–19,000 |
| tensile str, psi | 3,600–6,000 | 8,000–10,000 |
| tensile modulus, psi | 2.3–3.8 × $10^5$ | 3.5–5.0 × $10^5$ |

In the total prosthesis system, the cement functions as a boundary between the prosthesis and the bone and in this role greatly improves the load bearing capacity of the prosthesis compared with the condition without cement.

The modulus of the femoral component (metal) is approximately 15 to 35 million psi. Cement modulus is approximately 230,000 to 380,000 psi, and the modulus of the cancellous bone adjacent to the cement is approximately 10,000–70,000 psi. The order of decreasing modulus is Em to Ec to Eb. This situation then dictates that complex dynamic stresses (and strains) generated during normal body functions are transmitted through the prosthesis to the cement and ultimately to the bone.

The major long term complication of such prosthetic work is loosening of the prosthesis. Such failure frequently begins to appear 3 to 5 years after surgery.

Currently, an unconstrained ultra-high molecular weight polyethylene (UHMWPE)/metal alloy prosthesis, fixed with acrylic cement, offers the most resistance to loosening over other prosthesis systems. However, even with these improved systems, loosening still remains the most prevalent cause of joint replacement failure.

Loosening can occur in any one of the three areas:
1. Prosthesis/Cement
2. Cement/Cement
3. Bone/Cement 1. Failure at the prosthesis/cement interface occurs when relative motion exists between these two components. In the total hip system this is often seen with the femoral metal component.
2. Failure within the cement is due to fracture of the cement. This type of behavior has been noted with acrylic cement.
3. Failure at the bone/cement interface is the most common cause of loosening and, in part, may be traced to the behavior of living tissue in direct contact with a foreign body (implant). Bone is extremely stress sensitive: too little stress or too much stress will cause bone resorption (bone retreating from the interface with cement) leading to loosening. Between the limits of too little or too much, intermittent stress will provoke bone formation. The stress generated in the prosthesis and transmitted through the cement to the bone/cement interface will determine the reaction of the bone to the prosthesis. If the stress is well distributed and is within physiological limits bone will be formed and retain vitality.

Although acrylic bone cement does help to distribute the load, therefore lowering the overall stress level, this load distribution is not necessarily uniform and high stress points can occur particularly in the region of the lesser trochanter and the calcar. The cancellous (plate or honeycomb-like) bone functions quite effectively as a skeletal shock absorber in its natural state. Furthermore, the shock absorbing abilities of cancellous bone are totally dependent upon the bending and deformation of the trabecular (plate) arrangement. Filling the narrow space between trabecular bone with a high modulus material like acrylic cement seriously stiffens the trabecular bone and decreases the ability of the trabecular plates to bend and buckle. This, coupled with the high stresses transmitted to the bone/cement interface, often results in boney fracture which results in loosening of the prosthesis.

In summary, clinical observations have shown that the majority of total joint replacement failures (excluding failures due to poor surgical technique or infection) are directly or indirectly related to the functional deficiencies of acrylic cement previously known to the art.

Several approaches have been proposed by previous workers to *increase fracture resistance*, and prolong fatigue life.

An approach taken to improve the fracture behavior of the cement has been the *incorporation of fibers*. However, the reported studies in this area have revealed few instances where the fracture resistance has been significantly improved. On the other hand, this approach invariable brings about an increase, not a decrease, in the cement modulus. Furthermore, the fibers cause a drastic reduction in the cement's flow characteristics which can result in a poor mechanical interlock with the bone in actual use.

Still another suggestion has been to try to lessen the cement's residual stresses. These stresses arise from the shrinkage of the material during the polymerization and subsequent cooling in situ. When such stresses exist, the cement will internally fracture under lower loads than it would otherwise.

It is to be realized that this discussion of the background of the invention is necessarily made with a full knowledge of the invention to be disclosed below and is not meant to be construed as a view of the prior art as it may be construed by one having no prior knowledge of this invention.

SUMMARY OF THE INVENTION

It is a primary object of this invention to provide a novel orthopaedic bone cement composition which is prepared from a combination of monomer and polymer so as to provide a suitable elastic modulus, good toughness and good resistance to fracture.

It is another object of this invention to provide orthopaedic bone cements in accordance with the foregoing object which can exhibit accepted handling characteristics and toxicologic response.

It is a further object of this invention to provide an improved process of implanting prosthetic devices adjacent to porous bone structure.

Other objects of the invention will be obvious to those skilled in the art on their reading of this disclosure.

According to this invention an orthopaedic bone cement formulation is prepared from a mixture of methyl methacrylate monomer and a polymer which is rubbery or elastomeric. The polymer maybe formed from a ester or esters of acrylic or methacrylic acid. The liquid monomer and the polymer powder are packaged as two sterile components.

One component is packaged as an ampule containing 10 ml or 20 ml of the following composition:

| Methyl methacrylate monomer | 99–97% volume % |
|---|---|
| N,N—dimethyl-p-toluidine | 1–3% volume % |
| Hydroquinone | 75 ± 20 ppm |

The second component is a plastic pouch containing 20 gms or 40 gms of powder having the following composition

| (Radiolucent and Radiopaque): | |
|---|---|
| Radiolucent: | |
| Homo or copolymer of an ester or esters of acrylic or methacrylic acid | 99.5–97.0% by weight |
| Benzoyl peroxide | 0.5–3.0% by weight |
| Radiopaque: | |
| Homo or copolymer of an ester or esters of acrylic or methacrylic acid | 89.5–87.0% by weight |
| Barium sulfate USP | 10.0% by weight |
| Benzoyl peroxide | 0.5–3.0% by weight |

The monomer component of the orthopaedic cement is prepared in a fashion which is known and accepted in the present art.

The polymer component is prepared by a polymerization process through the incorporation of a free radical initiator in the amounts of from 0.01 to 2.0% by weight of the entire composition at reaction temperatures from 25° C. to 125° C. Suspension polymerization procedures can be used to produce small polymer spherical beads which can be used directly in this form. Alternately, bulk polymerization may be used to produce a large polymer mass which is then ground to the proper particle size distribution before use. Often times it is useful to blend spherical polymer beads when ground polymer to impart proper cement handling characteristics.

It is a feature of this invention that the polymer powder component of the cement have a glass transistion temperature (Tg) below the body temperature (about 37° C.). When implanted in the body, the cement is a composite material consisting of relatively rubbery polymer particles embedded in a rigid glassy matrix of polymethyl methacrylate. The toughness and fracture resistant properties of this cement are derived from this rubbery dispersed polymer phase. Handling characteristics such as consistency, working time and setting time are dependent on the solubility of the polymer phase in methyl methacrylate monomer and the concentration of initiator and activator. Solubility of the polymer phase is regulated by the chemical and physical structure of the polymer. Solubility can be adjusted by copolymerization or by varying the degree of cross-linking. The concentration of initiator and activator are advantageously selected so as to provide a setting time of about 10 to 15 minutes.

Some compatibility at the interface between rubbery particles and the primary acrylic resin, e.g. the polymerized MMA resin, is desirable. Therefore, it has been found particularly advantageous to utilize an acrylate or methacrylate based polymer particle with the methacrylate-based primary resin.

However, as those skilled in the art realize, these particles play what is primarily a mechanical role. Nevertheless, they must be compatible with the methacrylate-based primary resin; and meet toxicologic requirements. Consequently, acrylates and methacrylates are particularly desirable.

Orthopaedic cements disclosed in this invention are supplied as a two component system which are mixed during surgery, just prior to insertion.

The monomer component is prepared from distilled methyl methacrylate monomer, distilled N,N-dimethyl-p-toluidine and purified hydroquinone. These components are mixed in the proper ratio and sealed in an ampule as a sterile unit.

The novel polymer(s) utlized as the powder component of the orthopaedic cement can be prepared from one monomer (homopolymer) or from a combination of two or more monomers (copolymer, terpolymer, etc). There are three basic requirements such polymers must meet in order to impart the desired properties to the orthopaedic cement:

Glass transition temperature below 37° C.
Non-tacky polymer particles
Proper solubility in MMA The glass transition temperature of the polymer component must be below 37° C. to ensure the rubbery nature of the dispersed phase in the cement.

The polymer component must be a free flowing powder (nontack) to impart the proper handling and/mixing characteristics to the cement. Moreover, the powder advantageously has an ultimate elongation of at least about 90%, preferably 120% or more, and a tensile modulus of at least 20 psi; preferably about 300 psi or more.

The solubility of the polymer component in methyl methacrylate monomer must be similar to the currently utilized PMMA powders. This will ensure the proper working time and handling characteristics of the improved cements.

Polymers which satisfy the above mentioned criteria will impart the necessary qualities to the orthopaedic cement, namely, lower modulus, increased toughness, increased resistance to fracture and conventional handling characteristics.

Polymerization under standard suspension or bulk polymerization techniques, as known in the art for vinyl monomers, can be used to produce the polymer component of the cement. The free radical initiated reactions are preferred at conventional temperatures to ensure high conversion of the monomer(s) to polymeric form.

The monomers most useful in this invention preferably have the following formula:

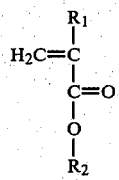

where $R_1$ is selected from the class of hydrogen or methyl group, $R_2$ has one to twenty carbons and is an alkyl group, substituted alkyl group, oxa-alkyl group, aromatic group, or siloxanyl alkyl group.

Another criteria useful in selecting the polymeric component is the differential between the solubility parameters of the matrix monomeric system and the polymer of which the powder is made. It is preferred that the polymeric component have a solubility parameter within about 0.2 units of that methyl methacrylate and preferably a maximum difference of about 0.1 units.

Representative acrylates and methacrylates monomers and their corresponding polymers which could be utilized in this invention include:

| Polymer (Acrylates) | $T_g$, °K. |
|---|---|
| Poly (Benzyl acrylate) | 279 |
| Poly(n-Butyl acrylate) | 219 |
| Poly(sec-Butyl acrylate) | 251 |
| Poly(Dodecyl acrylate) | 270 |
| Poly(2-ethoxyethyl acrylate) | 223 |
| Poly(2-ethoxypropyl acrylate) | 218 |
| Poly(Ethyl acrylate) | 249 |
| Poly(2-ethylbutyl acrylate) | 223 |
| Poly(2-ethylhexyl acrylate) | 223 |
| Poly(2,2,2-trifluoroethyl acrylate) | 263 |
| Poly(Heptyl acrylate) | 213 |
| Poly(2-heptyl acrylate) | 235 |
| Poly(Hexyl acrylate) | 216 |
| Poly(Isopropyl acrylate) | 267 |
| Poly(3-methoxybutyl acrylate) | 217 |
| Poly(2-methoxyethyl acrylate) | 223 |
| Poly(3-methoxypropyl acrylate) | 198 |
| Poly(Methyl acrylate) | 283 |
| Poly(2-methylbutyl acrylate) | 241 |
| Poly(3-methylbutyl acrylate) | 228 |
| Poly(2-methylpentyl acrylate) | 235 |
| Poly(Nonyl acrylate) | 215 |
| Poly(Octyl acrylate) | 208 |
| Poly(2-octyl acrylate) | 228 |
| Poly(3-pentyl acrylate) | 267 |
| Poly(Phenethyl acrylate) | 270 |
| Poly(Propyl acrylate) | 236 |
| Poly(Pentamethyldisiloxanyl methyl acrylate) | <37 |
| Poly(Pentamethyldisiloxanyl ethyl acrylate) | <37 |
| Poly(Pentamethyldisiloxanyl propyl acrylate) | <37 |
| Poly[Tris(trimethylsilyl)siloxanyl propyl acrylate | <37 |

| POLYMER (Methacrylates) | $T_g$, °K. |
|---|---|
| Poly(Butyl methacrylate) | 293 |
| Poly(Decyl methacrylate) | 203 |
| Poly(Dodecyl methacrylate) | 208 |
| Poly(2-ethylhexyl methacrylate) | 263 |
| Poly(Hexadecyl methacrylate) | 268 |
| Poly(3,5,5-trimethylhexyl methacrylate) | 274 |
| Poly(Octadecyl methacrylate) | 173 |
| Poly(Octyl methacrylate) | 253 |
| Poly(3-oxabutyl methacrylate) | 289 |
| Poly(Pentyl methacrylate) | 268 |
| Poly(Phenethyl methacrylate) | 299 |
| Poly(Pentamethyldisiloxanyl methyl methacrylate) | <37 |
| Poly(Pentamethyldisiloxanyl ethyl acrylate) | <37 |
| Poly(Pentamethyldisiloxanyl propyl acrylate) | <37 |
| Poly[Tris(trimethylsilyl)siloxanyl propyl acrylate | <37 |

It should be understood that the homopolymers listed above do not limit this invention since many useful combinations of the above listed monomers are possible. In fact, the solubility properties of the polymer component of the cement can be tailored by copolymerizing two, three or more of the above listed monomers. In certain cases it may also be possible to copolymerize a minor amount of an acrylate or methacrylate monomer not listed above (one whose homopolymer has a glass transition temperature above 37° C.) with one or more of the above listed monomers to form a copolymer with a glass transition temperature below 37° C.

It is well known that the solubility of a polymer can be substantially altered by including a crosslinking (di, tri or higher functionality) monomer in the formulation. The polymer powder component disclosed in this invention may be crosslinked for just such a reason. The cross-linking monomer would be added to the other monomer(s) in the formulation and polymerization carried out in the prescribed fashion to yield a crosslinked polymer mass. Examples of such crosslinking agents include polyfunctional derivatives of acrylic acid, methacrylic acid, acrylamide, methacrylamide and multivinyl substituted benzene including, but not limited to, the following: ethylene glycol diacrylate or dimethacrylate diethylene glycol diacrylate or dimethacrylate tetraethylene glycol diacrylate or dimethacrylate polyethylene glycol diacrylate or dimethacrylate trimethylolpropane triacrylate or trimethylacrylate Bisphenol A diacrylate or dimethacrylate ethoxylated Bisphenol A diacrylate or dimethacrylate pentaerythritol tri- and tetraacrylate or methacrylate tetramethylene diacrylate or dimethacrylate methylene bisacrylamide or methacrylamide dimethylene bisacrylamide or methacrylamide N,N'-dihydroxyethylene bisacrylamide or methacrylamide hexamethylene bisacrylamide or methacrylamide decamethylene bisacrylamide or methacrylamide divinyl benzene.

The polymer powder component of the cement can be prepared in any number of ways known in the art, such as bulk polymerization, solution polymerization or suspension polymerization. The preferred method would be suspension or bulk polymerization. With suspension polymerization polymer beads of pearls of the proper size distribution are prepared, washed and purified and used directly in this form as the polymer component of the cement. With bulk polymerization the polymer is formed in any convenient vessel, then ground to a finely divided state, classified to the proper size distribution. Generally, the powder component of the orthopaedic cement is not 100% ground material but either 100% bead or pearl or a combination of beads with ground material.

The polymer powder component of the cement is mixed with a finely divided initiator such as benxoyl peroxide, packaged and sterilized by gamma irradiation.

Although benzoyl peroxide is the most commonly utilized initiator in orthopaedic cements other peroxides could also be used. The following is a list representative peroxides that are of interest as the initiator component of the cement formulation:

benzoyl peroxide
    lauroyl peroxide
    methyl ethyl peroxide
    diisopropyl peroxy carbonate The activator component of the orthopaedic cement is commonly N,N-dimethyl-p-toluidine, however, in general the tertiary amines, as a class, will actively promote peroxide decomposition. Since N,N-dimethyl-p-toluidine, is only one member of this chemical class other, similar compounds, such as N,N-dimethyl aniline, would also serve as acceptable activators in the cement formulation. In addition, sulfinic acid has been reported to serve as an activator in the current cement systems.

ILLUSTRATIVE EXAMPLE OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that orders skilled in the art will more fully understand the invention and the principles thereof and will be able to modify it and embody it in a variety of forms, each as may be best suited in the condition of a particular case.

EXAMPLE I

A bone cement formulation is prepared in the following manner:

Component A:

A solution is prepared from freshly distilled methyl methacrylate (MMA) and N,N-dimethyl-p-toluidine (DMT) with hydroquinone (HQ) as an inhibitor. The proportions are as follows:

MMA 98% v/v
    DMT 2% v/v
    HQ 75 ppm

Component B:

Suspension polymerized (bead) n-butyl methacrylate obtained from Polysciences, Inc., serves as the powder component. This polymer material is characterized by the following physical properties using the conventional procedures of ASTM D-638 using a X-head speed of 2 inches per minute at 25° C.

Stress at Break—80 psi
    Ultimate Elongation—160%
    Tensile Modulus—400 psi

The cement is prepared by dissolving 0.8 gms of benzoyl peroxide in 20 ml of Component A solution, then quickly cooling the liquid to $-50°$ C. in a dry ice/acetone bath. Once cooled the solution is added to 40 gms of Component B in a mixing bowl, then stirred for about two minutes.

A test specimen was prepared by poring the resulting material into a frame mold ($6'' \times 6'' \times 0.1''$) and covering with a plate bearing a coat of stick resistant polymer "(Teflon)". The frame mold, sandwiched between two such Teflon chad plates is placed in a hydraulic press and approximately a 25 pound load (0.7 psi) is applied. The mold is vented (opened/reclosed) after 30 seconds. After one hour under positive pressure the polymerized, nearly void free, cement plaque is removed from the mold.

EXAMPLE II

This example illustrates the lower modulus and impoved toughness attained with the novel cement system as compared to conventional cements.

Cement plaques were prepared by the method outlined in Example I. The only exceptions were the inclusion of barium sulfate ($BaSO_4$) and the use of room temperature monomer with the conventional cements while the novel cement monomer component was cooled, as stated. After preparation, the test plaques were conditioned at room temperature for 48 hours prior to testing. Tensile samples were taken from tthe plaques and conditioned at 37° C.$\pm 1°$ C. for 24 hours before testing. The tensile testing was run in accordance with ASTM D-638 gauge length: 2.0 in.
    cross head speed: 0.2 in/min.
    extensometer: 100× amplification
    temperature: 37° C.

The cements tested were:

SIMPLEX P: Surgical grade orthopaedic cement containing 10% BaSO$_4$ supplied by HOMEDICA, INC., Rutherford, N.J.

DUZALL: A dental grade PMMA cement similar to orthopaedic types, with 10% BaSO$_4$ added. Supplied by CORALITE DENTAL PRODUCTS, Chicago, Ill.

Novel cement disclosed in Example I based on poly(n-butyl methacrylate) powder component with 10% BaSO$_4$ added.

The tensile properties of the cements tested are listed in TABLE I. It can be seen that total replacement of the PMMA powder component with poly(n-butyl methacrylate), PnB.M., produced a cement with a significantly lower modulus (3 to 5 times lower) than either of the conventional cements based on a PMMA powder component. The elongation to break was improved well over ten times and the toughness was increased 5 to 15 fold.

TABLE I

| | Yield Str. dynes/cm$^2$ | Modulus dynes/cm$^2$ | Elongation % | Toughness* |
|---|---|---|---|---|
| SIMPLEX P | 3.2 × 10$^8$ | 10.3 × 10$^{10}$ | 4.1 | 2 |
| DUZALL (+ 10% BaSO$_4$) | 3.2 × 10$^8$ | 7.0 × 10$^{10}$ | 6.9 | 6 |
| PnBM (+ 10% BaSO$_4$) | 1.4 × 10$^8$ | 2.1 × 10$^{10}$ | 90.0 | 30 |

*Index based on the area under the stress/strain curve

EXAMPLE III

This example illustrates the improved fracture resistance attained with the novel cement system as compared to conventional cements.

Cement plaques were prepared by the methods outlined in EXAMPLE I and II. The flexural testing was performed at room temperature and in accordance with ASTM-D790 method I.

sample: 3"×0.5"×0.1"
support span: 1.6 in

Surface energy tests were carried out in accordance with the method described by Johnson [Journal of Applied Physics 43, 1311 (1972)].

sample: 2.5"×0.9"×0.1"
guage length: 1.0 in
cross head speed: 4.0 in/min.
temperature: 37° C.

The surface energy is defined as $$\alpha = \frac{\sigma^2 \pi c (1 - \nu^2)}{2E} = ERGs/cm$$

where:
σ = breaking stress
C = crack length
ν = poissons' ratio (0.32)
E = modulus of elasticity (three point bending)

Fracture measurements were carried out on SIMPLEX P, DUZALL, DUZALL (+10% BaSO$_4$), PnBM and PnBM (+10% BaSO$_4$) with the results summarized in TABLE II. The fracture surface energy measurements indicate that the basic PnBM system (no BaSO$_4$) is more than ten minutes as fracture resistant as either of the conventional cements. The addition of BaSO$_4$ to either DUZALL or PnBM reduces the fracture resistance of each, however the fracture resistance of the PnBM (+10% BaSO) maintains a twofold superiority.

TABLE II

| Cement System | Fracture stress dynes/cm$^2$ | Flexural modulus dynes/cm$^2$ | Fracture surface energy (ERGs/cm$^2$) |
|---|---|---|---|
| SIMPLEX P | 13.4 × 10$^7$ | 3.6 × 10$^{10}$ | 0.2 × 10$^5$ |
| DUZALL | 10.0 × 10$^7$ | 3.5 × 10$^{10}$ | 1.2 × 10$^5$ |
| DUZALL (+ 10% BaSO$_4$) | 8.0 × 10$^7$ | 3.4 × 10$^{10}$ | 0.8 × 10$^5$ |
| PnBM | 20.4 × 10$^7$ | 1.1 × 10$^{10}$ | 16.0 × 10$^5$ |
| PnBM (+ 10% BaSO$_4$) | 8.4 × 10$^7$ | 1.5 × 10$^{10}$ | 2.0 × 10$^5$ |

It is also to be understood that the following claims are intended to cover all of the generic and specific features of the invention herein described and all statements of the scope of the invention which might be said to fall therebetween.

What is claimed is:

1. An improved orthopaedic cement comprising acrylate matrix polymer together with a powder formed of a second acrylate polymer which second polymer has a solubility parameter within about 0.2 units from the monomer from which said matrix polymer is formed, which has a glass transition temperature below human body temperature (37° C.) and which, at said human body temperature, is substantially more extensible than said matrix polymer:

said cement, when implanted in the human body, at body temperature being a composite material consisting of relatively rubbery polymer particles embedded in a rigid, glassy matrix of polymethyl methacrylate and having a setting time of about ten to fifteen minutes.

2. The cement of claim 1 wherein said matrix polymer is polymethlymethacrylate and said powder is formed from a polymer having an elongation of at least 90%, and a tensile modulus of at least 200 psi.

3. The cement of claim 1 wherein said matrix polymer is polymethlymethacrylate and said powder is formed from a polymer having an elongation of at least 120%, and a tensile modulus of at least 300 psi.

4. A cement as defined in claim 1 wherein said powder is poly n-butyl methacrylate.

5. A cement as defined in claim 1 wherein said cement withstands a stress of fracture stress of about 20 × 10 dynes/cm$^2$ and has a modulus of less than about 2 × 10$^{10}$ dynes/cm$^2$.

6. A cement as defined in claim 1 wherein said cement comprises an x-ray opacifying quantity of filler and a modulus of less than about 2 × 10$^{10}$ dynes/cm$^2$.

7. A cement as defined in claim 1 wherein the solubility parameter of polymerizable material from which said matrix is formed and said powder polymer are within about 0.2 units and wherein said cement withstands a fracture stress of about 20 dynes/cm$^2$ and has a modulus of less than about 2 × 10$^{10}$ dynes/cm$^2$.

8. An orthopaedic cement as specified in claim 1 wherein:

said relatively rubbery polymer is cross-linked n-butyl methacrylate polymer.

9. An orthopaedic cement as specified in claim 1 wherein:

said relatively rubbery polymer is a co-polymer of n-butyl methacrylate and tris (trimethylsilyl) siloxanylpropyl acrylate.

10. An orthopaedic cement comprising, at human body temperature, a relatively rubbery polymer in a rigid matrix polymer:

said relatively rubbery polymer being poly n-butyl methacrylate which in use condition has an elongation of at least 90%, a tensile modulus of at least 200 psi and a glass transition temperature below said human body temperature (37° C.):

said rigid matrix polymer being polymethyl methacrylate;

the solubility parameters of said rigid matrix polymer and said relatively rubbery polymer being within about 0.2 units;

and said cement being characterized by withstanding a fracture stress of about 20 dynes/cm$^2$, having a modulus of less than about $2 \times 10^{10}$ dynes/cm$^2$,; including an X-ray opacifying quantity of filler and having a setting time of ten to fifteen minutes.

* * * * *